ns Patent [19]

United States Patent [19]

Dannelly

[11] 4,177,255
[45] Dec. 4, 1979

[54] RUMEN-STABLE PELLETS

[75] Inventor: Clarence C. Dannelly, Kingsport, Tenn.

[73] Assignee: Eastman Kodak Company, Rochester, N.Y.

[21] Appl. No.: 830,279

[22] Filed: Sep. 2, 1977

[51] Int. Cl.$^2$ .......................... A61K 9/24; A61K 9/32; A61K 9/36

[52] U.S. Cl. ........................................ 424/21; 424/16; 424/19; 424/22; 424/31; 424/32; 424/33; 424/35

[58] Field of Search .................. 424/16, 19, 21, 22, 424/31, 32, 33, 35

[56] References Cited

U.S. PATENT DOCUMENTS

| | | |
|---|---|---|
| 3,692,562 | 9/1972 | Kawata et al. ........................ 424/32 |
| 3,829,564 | 8/1974 | Merry et al. ........................... 424/32 |
| 3,832,252 | 8/1974 | Higuchi et al. ......................... 424/19 |
| 3,880,990 | 4/1975 | Bauer et al. ............................ 424/19 |
| 3,917,813 | 11/1975 | Pedersen ................................ 424/19 |
| 3,935,326 | 1/1976 | Groppenbacher et al. ........... 424/32 |

Primary Examiner—Sam Rosen
Attorney, Agent, or Firm—John F. Stevens; Daniel B. Reece, III

[57] ABSTRACT

Pellets adapted to be orally administered to ruminants are disclosed. The pellets have a core comprising a nutrient and/or medicament, and a coating which protects the core in the environment of the rumen to allow utilization of the core in the abomasum and/or intestine. The coating comprises a polymeric matrix which is resistant to acid and a substance dispersed throughout the continuous matrix which is leachable from the matrix in the environment of the abomasum but not the rumen.

7 Claims, 5 Drawing Figures

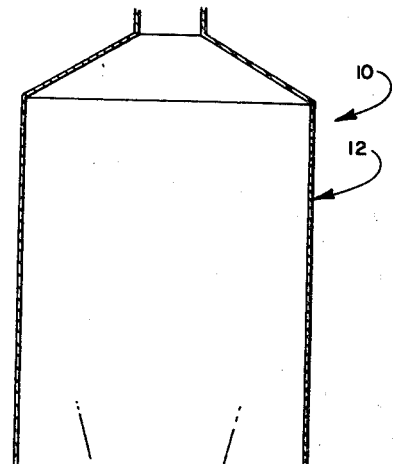
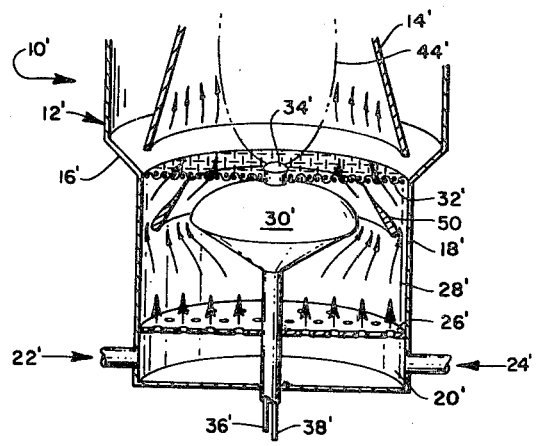
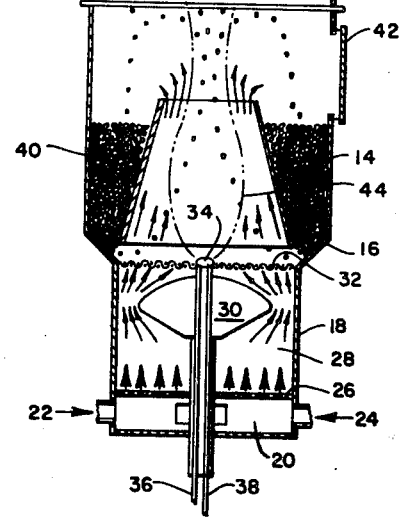
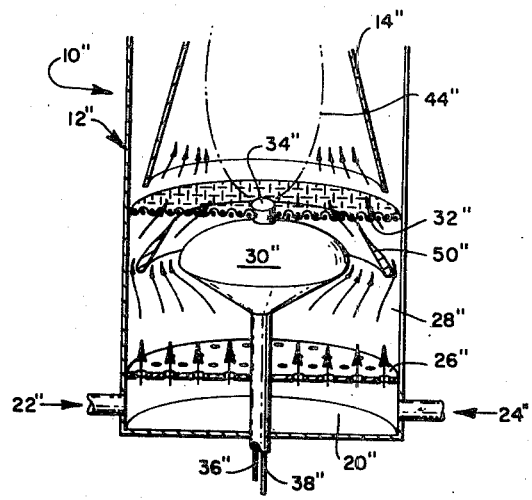
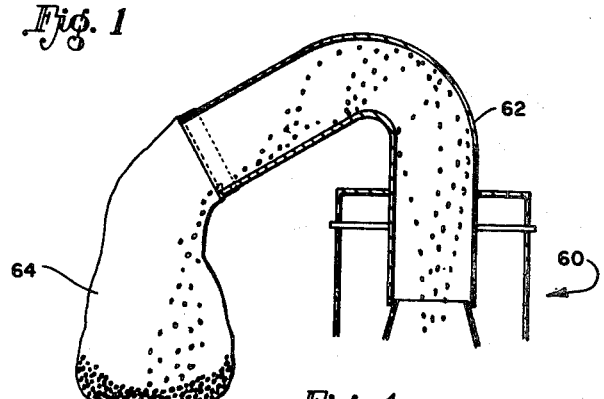

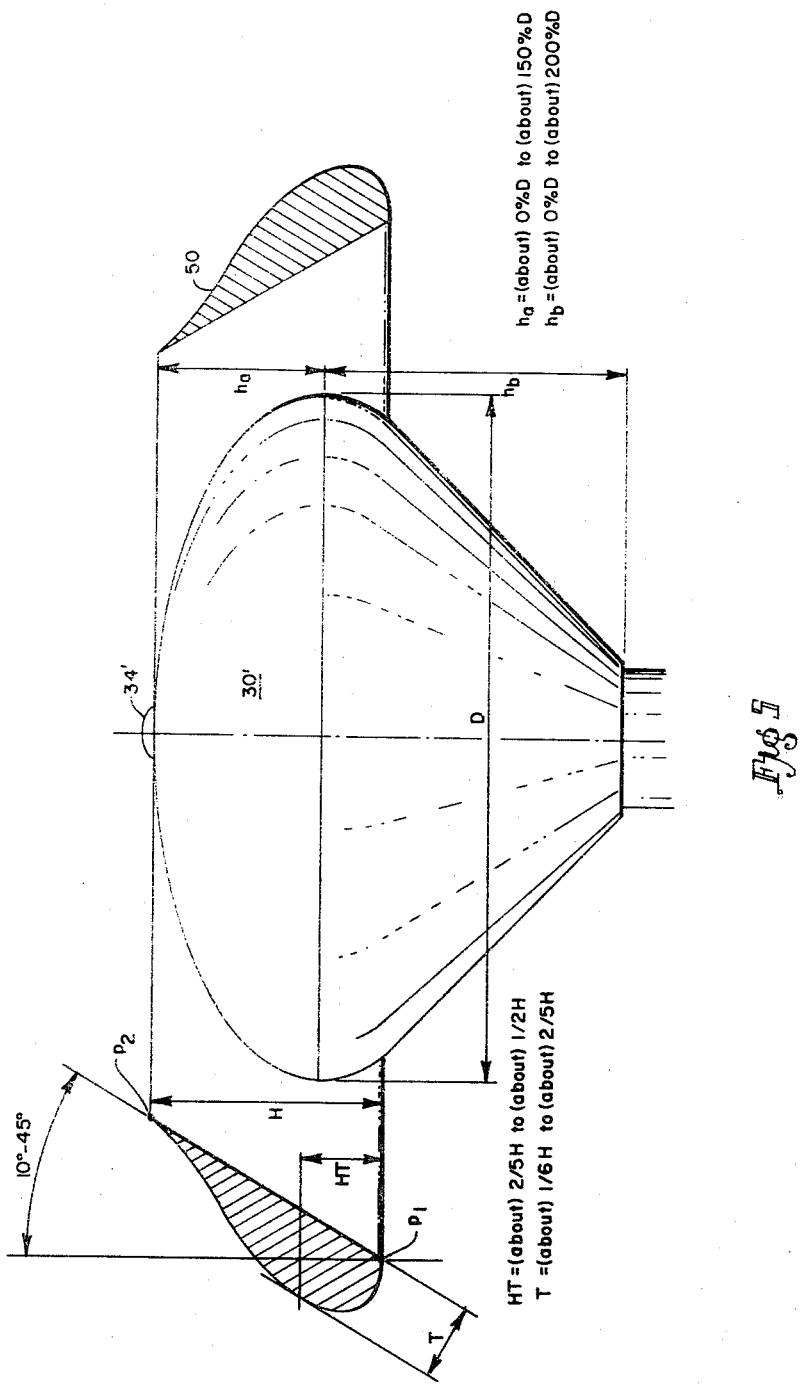

RUMEN-STABLE PELLETS

This invention relates in general to pellets adapted to be orally administered to ruminants and which are beneficial to ruminants after passing the rumen and reaching the abomasum and/or intestines. More particularly, this invention relates to pellets having, in terms of structure, a core material such as a nutrient or medicament, and an imperforate coating over the core material which protects the core in the environment of the rumen, but which loses continuity under the more acidic conditions of the abomasum to render the core material available for utilization by the animal.

In ruminants, ingested feed first passes into the rumen, where it is pre-digested or degraded by fermentation. During this period of fermentation the ingested feed may be regurgitated to the mouth via the reticulum where it is salivated and ruminated. After a period of fermentation regulated by natural processes and variable depending on the animal and the feedstuff, adsorption of digested nutrients starts and continues in the subsequent sections of the digestive tract by the ruminant animal. This process is described in detail by D. C. Church, "Digestive Physiology and Nutrition of Ruminants", Vol. 1, O.S.U. Book Stores, Inc., of Corvallis, Oregon.

The rumen, the largest of the four stomach compartments of ruminants, serves as an important location for metabolic breakdown of ingested foodstuffs through the action of microorganisms which are present therein. Ingested food is typically retained in the rumen for from about 6 to 30 hours or longer in some instances, during which time it is subject to metabolic breakdown by the rumen microorganisms. Much ingested protein material is broken down in the rumen to soluble peptides and amino acids and utilized by the rumen microogranisms. When the rumen contents pass into the abomasum and intestine, the microbial mass is digested, thus providing protein to the ruminant. Thus, the natural nutritional balance of the ruminant animal is primarily a function of the microbial composition and population.

In preparing nutrients and medicaments intended for administration to ruminants, it is important to protect the active ingredients against the environmental conditions of the rumen, i.e., microbial degradation and the effects of a pH of about 5.5, so the active substance will be saved until it reaches the particular location where adsorption takes place. It is well known that the rate of meat, wool and/or milk production can be increased if sources of growth limiting essential amino acids, and/or medicaments, are protected from alteration by microorganisms residing in the rumen and become available for direct absorption by the animal later in the gastrointestinal tract.

Materials which protect the core against degradation by the rumen contents should be resistant to attack by the rumen fluid which contains enzymes or microorganisms but must make the active ingredient available rapidly in the more acidic fluid of the abomasum at a pH within the normal physiological range of about 2 to about 3.5. To more easily coat or encapsulate active ingredients in protective materials, the protective materials should be soluble in certain organic solvents for coating purposes.

Because proteins are subject to breakdown in the rumen, it has been suggested that protein-containing nutrients fed to ruminants be treated so as to permit passage without microbial breakdown through the rumen to the abomasum. Suggested procedures have included coating the protein material, for example, with fats and vegetable oils; heat treating of the protein material; reacting the protein material with various compounds such as formaldehyde, acetylenic esters, polymerized unsaturated carboxylic acid or anhydrides and phosphonitrilic halides, etc.

It is well known that all proteins found in animal and plant life are chemical compounds containing different combinations of over 20 amino acids, the number and arrangement of such acids being fixed in any particular protein. Twelve of these amino acids can be synthesized in nutritionally adequate amounts from other substances by biochemical processes normally present in most animals, but the remaining 10 essential amino acids are not synthesized in sufficient quantities and must be ingested by the animal. Since the proportions of the constituent amino acids in a particular protein cannot be varied, the essential amino acid least in supply limits the amount of that protein which can be produced by the animal. Consequently, for any given diet, there will be a particular essential amino acid which limits the production of protein incorporating that essential amino acid unless, of course, two or more such amino acids are equally limiting.

The appreciation of the above principles leads to the formulation of diets for nonruminant animals which provide the optimum proportion of amino acids and have enabled significant increases in protein production to be achieved. In the ruminant, dietary proteins and amino acids are, to a variable extent, broken down to ammonia and various organic compounds by microbial fermentation in the first two compartments of the stomach (the rumen and reticulum). The bacteria and protozoa in these organs utilize these metabolites for their own growth and multiplication and the microbial protein so formed passes on to the abomasum, the compartment of the stomach corresponding to the stomach of nonruminants, where it is partially digested. The process is completed in the small intestine and the amino acids are absorbed.

It is likewise well-known that medicaments are more effective when they are protected from the environment of the rumen. See, for example, U.S. Pat. Nos. 3,041,243 and 3,697,640.

According to this invention, a coating or film forming material provides protection and release characteristics for the core material, and includes a mixture or blend of at least one hydrophobic polymeric substance, insoluble in aqueous acidic media, and a substance dispersed therein which is subject to attack by aqueous acidic media. The polymeric substance is normally a continuous matrix. The dispersed substance may be organic or inorganic and capable of leaching from the polymer matrix or losing integrity in aqueous environments below pH about 4.

Difficulty has been encountered with known coated pellets in attaining the necessary characteristics of protection and release at efficiencies required in commercial applications. When pellets are coated in accordance with the present invention, a surprisingly high percentage of the coated pellets are found (1) to be protected in the environment of the rumen for the required time, and (2) to release the core material in the environment of the abomasum within the required time. It was unexpected that the coating described herein would demonstrate such an increased efficiency. For example, at least 60%, and normally at least 75% and frequently higher percentages of the pellet core material will be protected by the coating for the required time in the mildly acidic environment of the rumen and be released by the coating within the required time in the more acidic environment of the abomasum. This increased efficiency may be due to the acid sensitivity characteristics of the coating, the resistance to abrasion in handling and/or the resistance to sticking under relatively high heat and humidity conditions which may damage the coating.

The coating material has the ability to withstand environmental conditions of the rumen, and the ability to expose the core material of the pellet in the environment of the abomasum. Thus, the coating material is resistant to pH conditions of about 5.5 for at least about 24 hours. The coating material releases the core material upon exposure to abomasum environmental conditions having a pH of about 3.5 after a time of about 10 minutes to about 6 hours. The exposure of the core may occur by the coating becoming permeable to the fluids therein or by dissolving or disintegrating. Another requirement for the coating material is to have the ability to withstand storage conditions of relatively high heat and/or humidity without a significant amount of blocking.

BACKGROUND

U.S. Pat. No. 3,619,200 relates to chemically modifying pellets and/or using a surface coating therefor. Proteinaceous feed is protected from breakdown within the rumen by the modification of protein itself, by the application of a protective coating to the feedstuff, or by combination of both. Various polymers are disclosed in this patent including copolymers of vinylpyridine and styrene. Canadian Pat. No. 911,649 discloses treatment of proeteinaceous materials with substances which are capable of reacting with proteins to form a polymeric proteinaceous complex on the surface of the material or by treating the proteinaceous material with a polymer or copolymer of a basic vinyl or acrylic monomer. This patent also discloses the use of copolymers and terpolymers derived from essentially a basic substituted acrylate or methacrylate monomer and at least one ethylenically unsaturated compound as rumen stable coatings. U.S. Pat. No. 3,880,990 and British Pat. No. 1,346,739 relate to an orally administratable ruminant composition wherein a medicinal substance is encapsulated or embedded in a normally solid, physiologically acceptable basic polymer. The compositions are produced by dispersing a medicinal substance in a first solvent and adding thereto a second solvent which is miscible with the first solvent but in which the polymer and medicinal substance are substantially insoluble. There is no suggestion of modifying the polymer by the use of additives. U.S. Pat. No. 3,041,243 relates to coatings for oral medicaments. These coatings are water-insoluble but acid-soluble film-forming polymers. An example mentioned in this patent is 2-methyl-5-vinyl pyridine copolymerized with vinyl acetate acrylonitrile, methyl acrylate or styrene.

U.S. Pat. No. 3,697,640 relates to materials such as medicaments and nutrients for ruminants which are coated with nitrogen-containing cellulosic materials such as, for example, cellulose propionate morpholino butyrate. This patent, however, fails to suggest the use of any additives in the nitrogen-containing cellulosic material, and U.S. Pat. No. 3,988,480 relates to a proteinaceous feedstuff for ruminants which has been treated with acetic acid to render it rumen stable.

U.S. Pat. No. 3,383,283 relates to coating pharmaceutical pellets with a plurality of charges of fatty acid as a melt or in solution. The fatty acid may then be dusted with a fine inert powder such as talc. There is no suggestion of using a continuous matrix polymer.

U.S. Pat. No. 3,275,518 relates to a tablet coating composition comprising a film-forming resin or plastic and a hard water-soluble or water-dispersible substance. Stearic acid is mentioned as an optional water-insoluble wax which may be included as an additive. Additional materials such as dyes, pigments, water-insoluble waxes, plasticizing agents, etc., may also be added to the coating. However, the film-forming resin or plastic according to this patent is selected from the group consisting of poly(methylstyrene), methylstyrene-acrylonitrile copolymers, poly(vinylchloride), poly(vinyl butyral), pentaerythritol or alkyd esters of rosin or modified rosin and terpene derived alkyd resins. There is no suggestion of the polymers according to applicants' invention. In fact, the plastic or resin is described as water-permeable, and the coating apparently is not designed for ruminants.

U.S. Pat. No. 3,623,997 relates to a method of sealing polymeric material walls of minute capsules by treating the capsules with a waxy material. The wax is introduced in a solvent which is subsequently dried and the wax is left as a residue in the walls. The capsule walls shrink and lose solvent and then entrap the wax tightly as a sealing material. There is no indication, however, that the polymer coating is designed to function for ruminants, and the wax is used as a sealing material. Applicant's hydrophobic substance is dispersed in the polymer.

U.S. Pat. No. 3,073,748 relates to tablets coated with a solution of an amphoteric film-forming polymer. The polymer is described as one selected from the group consisting of copolymers of (a) vinylpyridines with (b) a lower aliphatic $\alpha,\beta$-unsaturated monocarboxylic acid of 3 to 4 carbon atoms and copolymers of (a), (b) and a neutral comonomer selected from the group consisting of methyl acrylate, acrylonitrile, vinyl acetate, methyl methacrylate and styrene. There is no suggestion of using a dispersed additive.

British Pat. No. 1,217,365 and Canadian counterpart No. 851,128 relate to a particulate feed additive composition for ruminants wherein each particle comprises one or more amino acids totally encased in a continuous film of protective material which is transportable through the rumen without substantial degradation therein but which releases the active substance posterior to the omasum when the particles have a density within the range of 0.8 to 2.0 and diameters in the range of 200 to 2,000 microns. Suggested as protective materials are fatty acid triglycerides such as hydrogenated vegetable and animal fats, waxes such as rice-brand wax, and resin wax blends which are emulsified and/or dissolved in the intestinal tract.

PELLETS

The pellets according to this invention are adapted for oral administration to a ruminant. The pellets are of a suitable size, such as between about 0.05 in. and 0.75 in. in diameter. Also, the pellets must be of suitable density, i.e., a specific gravity of between about 1 and 1.4, have acceptable odor, taste, feel, etc. The pellets include a core and a continuous, film or coating completely encapsulating the core. The shape is usually not critical, except the pellets are commonly spherical for ease in coating.

CORE MATERIAL

The core is of a material beneficial to the ruminant upon passing the rumen and reaching the abomasum and/or intestine. Normally, the core is a solid material which has been formed into particles, such as by pelletizing. The cores may then be rounded if desired, by conventional means, such as by tumbling. The core should have sufficient body or consistency to remain intact during handling, particularly during the coating operation. Suitable core materials include various medicaments and nutrients such as, for example, antibiotics, relaxants, drugs, anti-parasites, amino acids, proteins, sugars, carbohydrates, etc. The core may also contain inert filler material such as clay.

Some amino acids suitable for use as a core material, their pH and solubility are as follows:

| Amino Acids Solubility and pH of Saturated Solutions | | |
|---|---|---|
| | Solubility g./100 g. water at 25° C. | pH |
| DL - Alanine | 16.7 | 6.2 |
| L - Asparagine | 3.1 | 4.7 |
| L - Arginine | 21.6 | 11.8 |
| L(−) - Cystine | 0.01 | 3.7 |
| DL - Methionine | 4.0 | 5.7 |
| L(−) - Lencine | 2.0 | 4.8 |
| L(−) - Tyrosine | 0.05 | 7.3 |
| DL - Phenylalanine | 3.0 | 5.6 |

Proteins from various sources are valuable for practice of the invention. Generally, proteins are polymers derived from various combinations of amino acids. Proteins are amphoteric substances which are soluble or suspendable in aqueous media either more acidic or more basic that the particular protein being considered.

The core material may be made ready for coating by the following method. The nutrient and medicament or the like are mixed with water, binders, and sometimes inert inorganic substances added to adjust the specific gravity of the pellet and the resulting plastic dough-like mass is extruded or rolled to obtain suitable size particles. Adhesive binders are added to strengthen the pellet and can be nontoxic vegetable gums, starches, cellulose derivatives, animal gums and other similar substances well-known in the art of food thickening and tablet making. Inorganic additives used to adjust the pH or the specific gravity of the pellet include such substances as insoluble, nontoxic pigment-like materials such as metal sulfates, oxides and carbonates having a relatively high density. The final desirable range of specific gravity of the rumen protected pellets is from 1.0 to 1.4. After creating suitable size pellets by extrusion, rolling or other suitable means, the pellets are dried to remove the water. The pellets are then coated by contacting them with a solution of the protective coating material in a suitable solvent or mixture of solvents as hereinafter described. Typical solvents of value include lower alcohols, ketones, esters, hydrocarbons, and chlorinated hydrocarbons.

COATING

The coating material is capable of forming a continuous film around the core by the evaporation of solvent from the coating material. It has the ability to withstand environmental conditions of the rumen, and the ability to expose the core material of the pellet in the environment of the abomasum. Thus, the coating material should be resistant to pH conditions of greater than about 5 for from about 6 to about 30 hours. The coating material should release the core material after exposure to abomasum environmental conditions having a pH of about 2 to about 3.3. Release should occur within the residence time in the abomasum or later in the intestinal tract but at least within a time period of 6 hours after contacting pH 3.5 or less. The exposure of the core may occur by the disperse phase substance being leached from the polymer matrix, such as by dissolving, disintegrating, or extensive swelling. The coating material is physiolgically acceptable, i.e., the coating material should not interfere with the ruminants' healthy or normal body functioning.

Another requirement for the coating material is its ability to withstand storage conditions of relatively high heat and/or humidity without a significant amount of blocking or sticking. It should have a sticking temperature of greater than about 50° C. Sticking temperature is defined as the temperature at which an applied force of 0.25 Kg/cm$^2$ for 24 hours causes the coating of pellets to adhere to the coating of adjacent pellets strongly enough to cause rupture of the coating when the pellets are forceably separated. Also, the coating material is preferably soluble or dispersable in organic solvents having boiling points of between about 40° C. and 140° C. to permit conventional coating processes such as spray coating to be used. Particularly suitable solvents include methylene chloride, chloroform, ethanol, methanol, ethyl acetate, acetone, toluene, isopropanol or mixtures of these.

Said coating comprises from about 35% to about 65% by volume of dispersed substance and has a sticking temperature of at least about 40° C. Moreover, the coating may account for from about 5% to about 50% of the total weight of the pellet.

POLYMER MATRIX AND DISPERSED SUBSTANCE

The polymeric substances which are useful in the coatings of this invention include those which are physiologically acceptable and resistant to the acidic conditions of the rumen and abomasum, at the normal body temperature of ruminants, i.e., about 37° C. and normal variances thereof.

The polymeric material is at least one polymer, copolymer, or blend of polymers selected from the group consisting of polystyrene, poly(methyl methacrylate), poly(vinylchloride), copolymers of vinylidene chloride, poly(dimethylsiloxane), cellulose esters, polyesters made from dicarboxylic acids having from about 8 to about 22 carbon atoms and glycols of about 4 to about 16 carbon atoms, polyamides from amino acids having from about 8 to about 22 carbon atoms or from dicarboxylic acids having from about 8 to about 22 carbon atoms condensed with diamines having from about 4 to about 16 carbon atoms and polymethacrylates having silicone or fluorine substituted alcohol moieties of from 2 to 8 carbon atoms. Polystyrene and poly(methyl methacrylate) are preferred.

The acid-sensitive, organic or inorganic dispersed phase substances useful in this invention include nontoxic insoluble multivalent cation salts of phosphoric and phosphorous acids such as magnesium phosphate, basic magnesium phosphate, aluminum phosphate, magnesium phosphite, ferrous phosphate, ferric phosphate and calcium phosphate. Useful organic disperse phase materials include crosslinked particles of polymer containing from 3 to 14% nitrogen as basic amino groups, particles of polyelectrolyte complexes wherein a polymer containing basic amino groups is linked to a high molecular weight acid and preferably an acidic polymer to form an insoluble pulverizable composition, particles of polyelectrolyte complexes wherein an acidic polymer is linked to a high molecular weight amine and preferably an amino group containing polymer, and a multivalent cationic salt of an acidic polymer. The coating may also contain plasticizers, inert fillers, etc. In any case, the acid-sensitive, dispersed phase substance is present in an amount of between about 35 and 65% of the volume of the film, preferably from about 40 to 60%. Specific examples of useful disperse phase substances will be disclosed in the examples.

The acid sensitive, disperse-phase material is prepared and pulverized by grinding if necessary to obtain particles in the range of from 40 to 400 mesh. These particles are then mixed or blended with a suitable continuous matrix polymer, mixture of polymers or mixtures of plasticizers and polymers. The blending operation can be by any method known to the art of compounding paints and other protective coatings, but kneading the molten mass of polymer in contact with the particles and mixing the particles in a solution of the continuous matrix polymer are the preferred methods. If the blending is done using the hot melt kneading method, the polymer is then dissolved in a suitable solvent. Next pellets of nutritional or therapeutic value are coated by an atomized spray of the solution of polymer containing the dispersed and acid sensitive particles. The coating will normally account for from 5-50% by weight of the pellet.

CORE NEUTRALIZATION

Core materials may be raised in pH if necessary to a predetermined degree by mixing a basic neutralization substance therewith or by coating the core with a basic neutralization substance. The acidity is modified by adding nontoxic, insoluble, basic substances such as alkaline earth oxides, hydroxides, or carbonates, to the core material before the pallet forming step. Basic compounds of aluminum such as the various forms of hydrated alumina, aluminum hydroxide, and dibasic aluminum salts of organic acids, having less than 6 carbon atoms, such as dibasic aluminum acetate may also be used. These basic substances are added to the pellets by mixing the core material, basic substance, and binders as described above before adding water. The amount used depends on both the solubility and relative acidic nature of the proteinaceous substance, on the coating composition used to obtain rumen protection and on the thickness of the coating applied. Preferably, the pH of the core is at least 5.5, preferably to about 7.

When the core material is acidic, the water which permeates the film is believed to ionize the acidic groups and they in turn react with the amino groups in the polymer and in time disrupt the polymer from inside the capsule. When the core material is both soluble and acidic, both destructive forces operate and the protective film is quickly rendered ineffective as a rumen-stable coating.

At the same time, the solubility of the polymer at pH below about 3.0 has not been altered because, as an increment of polymer actually dissolves, the disperse phase hydrophobic substance is removed by ablative processes and eventually the polymeric film is destroyed. The theoretical function of the basic substance added to the core material is that is acts as a reserve of basicity. That is, any water which tends to ionize the acidity of the pellet also permits neutralization of such acidity and the attach on the protective film is prevented.

The core material may be neutralized by the following method. Nontoxic, insoluble basic substances such as oxides, hydroxides, carbonates, and basic salts of magnesium, calcium, and aluminum are blended with finely-divided nutrient and/or therapeutic substances at the time these are prepared for pelletizing. The amount of basic substance used, if any, depends on several interacting factors related to the relative acidity and/or solubility of the pellet, the time required for rumen protection, and the time required for release in the abomasum. Normally, the weight of basic substance, if used, will be within the range of 1-20% of the total weight of the core. In addition to the nutrient or therapeutic substance and the basic substance, the pellets may contain binders, density modifiers, and other minor ingredients required for special properties, as is common practice in the art of tablet making. In this practice of the invention, the various powdered ingredients are first dry blended to obtain a more or less homogeneous mixture, then water is added to obtain a plastic dough-like mass. The dough is then pelletized by extrusion, extrusion and tumbling, or by any method known to the art of pelletizing or tabletmaking. The water is removed by drying at ambient conditions, in heated ovens or fluidized beds. The dry pellets are then ready for subsequent coating operations performed by any method such as pan coating, fluidized bed coating, or spray coating or combinations thereof.

Another method of core neutralization is based on the concept that, whereas the coating is permeable to water and acidic water borne molecules, not all of the pellet interior is required to be neutralized. The nontoxic inorganic basic substances may be deposited on the surface of the core material prior to application of the coating. In practice, the preformed pellets are placed in a fluidized bed or other coating apparatus and a dispersion of an oxide, hydroxide, carbonate, or basic salt of magnesium, calcium, or aluminum in water or an organic liquid is sprayed on the pellet. The dispersion of basic substance preferably contains a binder and may also contain a protective colloidal substance wherein the ratio of binder plus protective colloidal substance to basic substance is less than about 1:3. If used, the amount of basic substance coated onto the pellet is normally from about 1 to about 20% of the weight of the core material. The binder and protective colloidal substance can be the same substance or different and are preferably soluble or dispersible in water and in the organic liquid used to suspend the basic substance. Such binder materials as relatively low molecular weight cellulose derivatives, synthetic polymers, and natural gums known to the art of tablet making are suitable for the practice of the invention. The organic liquid can be any having suitable solvent power and boiling in the range of from 40°-140° C.

APPLICATION OF COATING

In the practice of this invention, the polymeric material may conveniently be dissolved in a suitable organic solvent which would be physiologically acceptable in the event there are residues upon evaporation of the solvent, as hereinbefore described. The hydrophobic substance is blended in the solution, wherein the polymeric substance is a continuous matrix and the additives are dispersed therein. The coating solution may be applied by various well known means such as, for example, brushing, dipping, spraying, fluidized bed, etc.

A preferred apparatus and process for coating the cores will now be described.

In the drawings:

FIG. 1 is an elevation view in cross-section illustrating the apparatus and showing the gas flows and particle flow path from the annular bed to and through the truncated hollow cone and in return to the annular bed;

FIG. 2 is a partial elevation view in cross-section of a modified apparatus and illustrating the addition of an annular airfoil and showing the flow of gases relative to the aerodynamic structure and annular airfoil;

FIG. 3 is a partial elevation view in cross-section of another modified apparatus similar in all other respects to the modification shown in FIG. 2 except that the cross-section of the apparatus below the coating chamber is of the same diameter as that of the coating chamber;

FIG. 4 is a partial elevation view in cross-section of the upper portion of the apparatus of the invention for illustrating one possible manner of collecting the finally coated particles by use of an air porous bag; and FIG. 5 is a graphic illustration of the height, thickness and angular relationships of the annular airfoil with respect to the aerodynamic structure, and the height above ($h_a$) and height below ($h_b$) relationships of the aerodynamic structure to the greatest cross-sectional diameter of the aerodynamic structure.

The apparatus employs a truncated hollow cone in which the slope or pitch of the walls is such that the particles are accelerated at an increasing rate and not just at a rate so as to maintain the gas velocity at any given point in the cone at a level greater than that necessary to move the particles in a continuous upward direction. The slope or pitch of the walls would therefore appear to be more pronounced than the slope or pitch of the cone embodiment disclosed in the Larson et al patent. The significance of the slope or pitch of the truncated hollow cone of the invention is that when a particle first enters the cone at one rate of speed, it is then accelerated to a different rate of speed and continues to be accelerated to still different rates of speed as it moves upwardly through the cone. In this manner a separation is brought about between the particles so that after they are coated they may become sufficiently dry before coming into contact with other particles and thereby avoid undesirable clumping or agglomerating together. The pitch of slope is such as to cause a compression of the gas molecules and thereby cause the acceleration at an increasing rate.

In reference to FIG. 1, the coating apparatus is designated in general at 10 and includes a vertically disposed first hollow column 12 of regular shape. By "regular shape" is meant that it may be cylindrical, octagonal, hexagonal or of other configurations, so long as the hollow column is generally symmetrical with respect to its central axis. The hollow column contains therewithin the particle storage, coating, drying and deceleration zones, which will be described herein.

A truncated hollow cone 14, which may also be a tapered octagon or other tapered polygonal configurations, in other words, generally cone-shaped configurations, serving as an enclosure in which the upwardly flowing gases are received, compressed and accelerated, is centrally disposed within the first hollow column, has a uniformly decreasing cross-section in the upward direction and is of predetermined height dependent upon the size and weight of the particle to be treated. Within the truncated hollow cone in ascending order are the coating and drying zones. The cone serves also to separate the coating and drying zones from the deceleration zone, which lies in the region above the upper end of the cone, and from the storage zone, which lies therebetween the cone and the interior wall surface of the first hollow column.

The first hollow column 12 is provided at its lower end with an inwardly tapered base 16. The lower end of the truncated hollow cone is spaced radially inwardly from the inwardly tapered base.

A second vertically disposed hollow column 18 of regular shape is connected to the inwardly tapered base of the lower end of the first hollow column, the wall surface of the inwardly tapered base forms a juncture with the wall surface of the second hollow column.

Disposed within the second hollow column is a first plenum chamber 20 into which a suitable compressed gas, such as air, may be provided through two or more opposed inlets 22, 24; a gas or air collimating plate 26; a second plenum chamber 28 separated from the first plenum chamber 20 by the collimating plate 26; at least one gas shaping or aerodynamic structure 30 disposed within the second plenum chamber; and a particle support or supporting screen 32, which extends across the second hollow column and is located above the aerodynamic structure.

The gas or air collimating plate 26 is a perforated plate which causes the gas or air in the first plenum chamber to pass into the second plenum chamber in an essentially vertical and uniform flow, as illustrated by the vertical arrows.

The gas shaping or aerodynamic structure 30 in cooperation with the adjacent wall surface of the second hollow column, compresses and focuses the upwardly moving gas or air flow so that it flows over a portion of the surface of the aerodynamic structure, upwardly through the particle support screen and into the entrance end of the truncated hollow cone. The flow upwardly around the aerodynamic structure constitutes an annular flow, which adheres to the surface of the aerodynamic structure in the nature of a Coanda flow.

A spray nozzle 34 preferably extends above the top of the aerodynamic structure 30 through which is sprayed a suitable coating material. It is more convenient to have the spray nozzle located at the top of the centrally disposed aerodynamic structure. The coating material is supplied from a suitable source (not shown) through a conduit 36 extending up through the aerodynamic structure, and an atomizing gas may be supplied from a suitable source (not shown) through a conduit 38, also extending up through the aerodynamic structure, for subsequent mixing at the nozzle. The spray nozzle may also be pressure-operated rather than gas-operated.

The upper surface of the gas shaping or aerodynamic structure is centrally disposed within and extends generally horizontally across the cross-section of the vertically disposed hollow column. In other words, it has a cross-sectional plane generally perpendicular to the vertical axis of the vertically disposed hollow columns. The outer edge of the upper surface is equally spaced from the wall surface of the hollow column and defines therebetween with the wall surface of the hollow column a reduced pressure region for acceleration in velocity of the upwardly flowing gases in such manner that the upwardly flowing gases form a boundary layer that is directed away from the wall surface of the hollow column and that adheres to the upper surface of the gas shaping or aerodynamic structure for flow across a portion thereof.

The upper surface of the aerodynamic structure may be flat (not illustrated), but is preferably curved or approximately spherical as illustrated. It may have a height ($h_a$) above the cross-sectional plane (See FIG. 5), therefore, of from about 0% to about 150%, or preferably from about 10% to about 150% of the greatest cross-sectional diameter (D) (See FIG. 5) of the aerodynamic structure.

The surface below the greatest cross-sectional diameter may also be flat (not illustrated) and may therefore have a depth or height ($h_b$) below of from about 0% to about 200% of the greatest cross-sectional diameter (d) (See FIG. 5). Preferably, the surface below is formed in the manner disclosed in the drawings.

The aerodynamic structure as disclosed and as described is thus adapted to compress and accelerate the flowing gases near the periphery of the hollow column and direct them toward the center of the hollow column at an angle from about 10° to about 45° from a direction parallel to the flowing gases from the gas or air plenums.

The truncated hollow cone defines at its lower end a large diameter somewhat smaller than the diameter of the vertically disposed first hollow column, and has an increased diameter from about 0% to about 25% greater than that of the plane of the particle support screen. The lower end of the truncated hollow cone is spaced a predetermined amount from the screen and the upper end defines a diameter of from about 20% to about 80% of that of the lower end. The height of the cone ranges from about one to about six times the diameter of the lower end.

In operation, particles 40 may be suitably loaded into the coating apparatus 10, as through a closable opening at 42, into the storage zone lying between the wall surface of the first hollow column 12 and the outside wall surface of the truncated hollow cone 14. The particles are thus situated in an annular bed around the truncated hollow cone 14. The sloping outer wall surface of the truncated hollow cone, the inwardly sloping tapered base 16 of the first hollow column and the screen 32 serve to contain the particles in the annular bed prior to starting-up the coating operation.

The gas or air is turned on to start the circulation of the particles or pellets from the annular bed or storage zone into the coating, drying and deceleration zones and in return to the upper portion of the annular bed. The atomizing spray is then turned on and appropriately adjusted in a suitable manner by controls (not shown).

As previously pointed out, the Coanda flow or effect is named for the tendency of a fluid, either gaseous or liquid, to cling to a surface that is near an orifice from which the fluid emerges. Such "orifice" in this instance is formed in the region therebetween the closest approach of the aerodynamic structure to th adjacent side wall surface. The gas flow emerging from the "orifice" region around the aerodynamic structure is an annular flow which clings or adheres to the surface of the aerodynamic structure. The flow, therefore, from any one selected location around the "orifice" is opposed by the other flows so that it is prevented from continuing further over the upper surface of the aerodynamic structure by being forced upwardly away from the upper surface at some point for flow into the truncated hollow cone. A partial vacuum is formed in the region just above the upper surface of the aerodynamic structure and at the lower edge of the truncated hollow cone and this aids in the compression and focusing of the rising annular flow of gases. The upward flow is consequently caused to have a conical shape, as seen in phantom lines in FIG. 1 at 44 within the cone, and has a centering effect on the particle impelled upwardly through the cone.

As also pointed out, an important part of the Coanda effect is the tendency of the flow or gas or liquid to entrain, or draw in, more gas or liquid from the surrounding environment. In this latter manner, the particles are pulled from the annular bed or storage zone into the upwardly flowing gas due to the aforementioned partial vacuum or reduced pressure region that exists just above the screen adjacent the path of upward flow as a consequence of this Coanda effect. This reduced pressure or partial vacuum is directed perpendicular to the annular airflow from the "orifice". It is a different effect, however, from the horizontal shunting action occurring in the Wurster et al apparatus described above because there the horizontal shunting would extend not only toward the axis of the apparatus but also inefficiently toward the outer wall surface of the coating apparatus.

Once the particles are pulled into the upwardly flowing gas within the truncated hollow cone, they are impelled upwardly in an accelerating gas or air stream. As the particles pass through the lower central region or coating zone within the cone, they are contacted with an atomized spray coating of material. This atomized spray emerges from the spray nozzle 34 because the liquid coating substance is either forced through a single orifice designed to convert bulk liquids into droplets, or the liquid and an atomizing air stream emerge simultaneously from jets adjacent to each other. In either case, the fine droplets of coating material are in a flowable state, because the material is dissolved or melted in the region immediately above the spray nozzle.

Further up the truncated hollow cone, the liquid nature of the coating material, as deposited on the pellets or particles, changes to solid by evaporative or other solidification processes. During the transition from liquid to solid, the coated particles pass through a stage when they are sticky or tacky and would agglomerate if they contacted each other. This contact is prevented by the slope or pitch of the walls of the tuncated hollow cone and consequent accelerating boost of the particles to separate them in the manner previously discussed.

The conical nature of the cone causes a compression and acceleration of the rising column of gases and the upward velocity or acceleration of the particles occurs at an increasing rate as they rise in the cone. This acceleration causes an increasing vertical separation in space between the particles and therefore reduces the tendency for the particles to contact each other until the coating has become nontacky. It is this region of the cone that is thus called the "drying zone".

When the compressed gases and entrained particles pass upwardly out of the upper end of the cone, they expand into the larger area of the upper portion of the first hollow column and thus decelerate to a velocity too low to suspend the particles. This is the deceleration zone, where further drying takes place, and the particles then fall by gravity action to the annular bed where they gradually move down, also due to gravity, until they are pulled into the coating zone again. This recycling or recirculation continues until, based on previous experiments, a sufficient coating has been applied.

The atomized spray is turned off, and the gas or air entraining flow may be shut down or may be increased to drive the coated particles into the uppermost region of the first hollow column, as for collection in the manner illustrated in FIG. 4. Any other suitable manner of unloading the finally coated particles may also be used.

A coating apparatus having the design characteristics essentially as shown in FIG. 1, and having a diameter of eight (8) inches across the lower end and four (4) inches across the upper end of the truncated hollow cone, is charged with twenty-five (25) pounds of generally spherical pellets of animal feed supplement. The pellets are composed of 90% methionine and 10% binders. The average diameter of the spherical pellets is about 3 millimeter. About 250 standard cubic feet per minute of air at about 7 p.s.i.g. is admitted to the plenum chamber 20. This air causes a circulation of pellets through the truncated hollow cone 14, and the height of the cone above the support screen 32 is adjusted to obtain a pellet flow rate such that all the pellets in the annular storage zone move through the cone about once every minute. A coating solution is pumped through the spray nozzle 34 at the same time as 5 SCFM of atomizing air at 40 p.s.i.g. is supplied to the nozzle. The pumping rate is adjusted to pump one (1) pound of solution per minute. The apparatus is operated for about 45 minutes. The product is a pellet core coated with about a 2-mil layer of the polymer.

If the gases flowing upwardly around the aerodynamic structure could be seen as a series of layers of molecules, merely for sake of discussion, it is thought that there is an insignificant flow of molecules or layer or so of molecules along the interior wall surface of the second hollow column. By "insignificant" is meant that such layer or layers of molecules will not perform any supporting function of the particles in the annular bed.

Moving, therefore, radially inwardly from the interior wall surface of the second hollow, the more significant layers of molecules are caused to bend toward the gas shaping or aerodynamic structure, the innermost adhering to the surface of that structure as they pass upwardly through the "orifice" region. This adherence of the molecules to the surface of the aerodynamic structure may be favorably compared to the "teapot effect", which is a low-speed form of the "Coanda effect". When water is poured slowly from a glass, it tends to stick to the side of the glass in the same way that tea sticks to the spout of a teapot. High speed fluids behave similarly and adhere to a surface of suitable shape.

As the rising molecules flow over the surface of the aerodynamic structure after having passed the "orifice" region, previously mentioned, at some point along the upper surface of the aerodynamic structure the opposing character of the annular flow forces the molecules upwardly away from the upper surface as well as the adjacent molecule layers. A partial vacuum is created above the aerodynamic structure due to the high speed upward flow of gases, causing an inward bending of the upwardly moving molecules.

In the apparatus herein described, the particles move down in the annular bed by gravity without any "dancing" occurring, and are drawn into the upward flowing gases by the partial vacuum. Thus, any attrition that might occur is greatly minimized, and the overall operation is much more efficient.

In reference to FIG. 2 in which a modification is disclosed, the same reference numbers will be used to identify similar elements previously described, except that they will be primed to show that it is a different embodiment under discussion.

FIG. 2 represents an embodiment wherein the size of the coating apparatus 10' has been increased in order to handle larger batch loads of particles for coating treatment. It has been found that it is more practical to add an additional gas shaping or aerodynamic structure or an annular airfoil 50 instead of increasing the size of the aerodynamic structure 30'. In this manner, larger amounts of upwardly flowing gas or air may be supplied undiminished or unobstructed by a larger aerodynamic structure, and the annular airfoil serves to supplement the compression and focusing action on the upward gas flows so that substantially all gas flows move through the truncated hollow cone 14'.

Additional or multiple gas shaping or annular airfoils (not shown) also may be used for still larger coating apparatus. The exact shape and placement of the airfoils are functions of a number of variables. The most significant of the variables are size of the apparatus, size of the particle to be coated, density of the particle, rate of gas or air flow and the rate of recirculation of the particles through the coating zone desired.

In a larger-scale coating apparatus, therefore, one or more annularly shaped and placed gas shaping or aerodynamic structures or airfoils, angled or curved, may be provided concentric with and radially outwardly of the central gas shaping or aerodynamic structure. The annular airfoils may be attached to the central aerodynamic structure or to the walls of the coating apparatus by radial struts in such manner as to exert a minimum deflection of the upwardly flowing gases.

The annular aerodynamic structure is inwardly inclined in the upward direction so that its inclination lies in a plane extending about 10° to about 45°, as measured from the axis perpendicular to the diameter of the coating apparatus. The inwardly inclined annular structure provides a surface on which the gas or air impinges for subsequent shaping and direction upwardly into the truncated hollow cone.

The vertical height of the annular structure may be about 10–50% of the perpendicular cross section diameter of the coating apparatus.

In reference to FIG. 5, when the annular gas shaping structure has the configuration of an airfoil having at least one curved surface extending generally in the direction of gas flow, the overall angle of a line described from a point $p_1$, on the lower rim of the airfoil to a point, $p_2$, on the upper rim in the vertical direction, or perpendicular to a line which is tangent to the upper curved surface of the centrally disposed aerodynamic structure, is from about 10° to about 45° inward facing, as measured from the axis perpendicular to the diameter of the coating apparatus.

The cross-sectional configuration of an annular airfoil in a plane described from the center of the cross-sectional area of the coating apparatus to a point, $p_1$, on the lower rim of the airfoil to a point, $p_2$, in the upper rim of the airfoil is teardrop, or similar to the cross-sectional shape of a lifting aerodynamic shape, and having the thicker cross section on the forward part with reference to the direction facing the upwardly flowing gases. The thickest part is located about two-fifths (2/5) to about one-half (½) of the height in the vertical direction. In other words, the height (H) of the thickest part (T), or HT is equal to about 2/5 H to about ½ H. The thickest cross section (T) is from about one-sixth (1/6) to about two-fifths (2/5) of the height (H) of the airfoil; or T is equal to about 1/6 H to about 2/5 H.

The size, placement and geometrical configuration of the annular gas shaping structure are such, therefore, that the upwardly flowing gases are deflected radially inwardly at an angle from about 10° to about 45° from a direction parallel to the original gas flow.

In reference to FIG. 3, the same reference numbers will be used to identify similar elements previously described, except that they will be double-primed to show that it is still another different embodiment under discussion.

FIG. 3 represents an embodiment wherein the size of the coating apparatus 10″ has been increased to the same extent as that disclosed in the FIG. 2 embodiment. The embodiment in FIG. 3 differs from the embodiment in FIG. 2 in that the first and second hollow columns are disclosed as being co-extensive in cross-sectional diameter. In other words, the coating apparatus is disposed within a single hollow column. It could also be of smaller size so that only one gas shaping or aerodynamic structure 30″ is employed as in FIG. 1, instead of a size requiring the annular airfoil 50″.

The recycling or recirculation in this embodiment is necessarily faster because the particles are not as readily restrained in the annular bed region as they would be if there were an inwardly tapered base to assist in such restraint. Proportionately smaller batch loads may be used, therefore, since the recirculation of the particles is substantially continuous with the particles spending very little time in the annular bed. For this reason, an embodiment of this character is suitable for special purposes, while the embodiments of FIG. 1 and FIG. 2 are deemed to be of more general use.

In FIG. 4, this embodiment represents one manner of unloading a coating apparatus, and was briefly mentioned above with respect to one possible operation of the embodiment of FIG. 1.

Only the upper portion of a coating apparatus 60 is shown, and it could be used for any of the previously described embodiments. A conduit 62 is installed within the upper portion of the apparatus, as shown, and a gas or air porous collection 64 may be installed at the remote end of the conduit for collecting the finally coated particles in the manner already heretofore described.

In any of the embodiments described above, the truncated hollow cones may be adapted to be adjusted for movement upwardly or downwardly in a vertical plane. The same may also be accomplished with the aerodynamic structure, the annular airfoils and the spray nozzles, as desired to suit gas or air flows, particle sizes and weights, coating material consistencies and whatever other controlling factors may be concerned.

The particles or pellets to be coated may be batch-loaded and treated; or, if deemed advantageous, two or more such coating apparatus may be arranged in cascaded manner to provide for a continuous coating operation. The inlet for the particles in a cascaded arrangement may be disposed above the annular storage of one apparatus and the particles metered in predetermined manner into the annular storage bed, while the outlet to the next coating apparatus may be disposed on the opposite side of the annular storage bed and constitute a weir for outflow of excess coated particles. The inlet may also be disposed for gravity flow of particles to or into the annular storage bed. It may be desirable to provide for different coatings in different apparatus, or provide supplemental coatings.

Multiple spray nozzles may also be employed, as desired, to achieve different coating effects.

The examples which follow are submitted for a better understanding of the invention. While the examples are based on in vitro tests, the in vitro experiments shown in the examples simulate conditions existing in ruminants thereby permitting the study of coated pellets without the use of live animals. It has been determined by actual in vivo tests that the testing of pellets in the aqueous media used in the examples, simulating the environmental conditions of the rumen and abomasum with respect to temperature, pH, etc., provide reliable data concerning the protection offered by the coatings in the rumen, and releasability of the coatings in the abomasum. Nutrients such as amino acids and proteins which may be used in the core material are known to be beneficial to ruminants when positioned in the intestinal tract downstream from the rumen.

The fluid used to simulate environmental conditions of the rumen (at pH 5.5) is prepared by mixing 11.397 grams of sodium acetate with 1.322 grams of acetic acid and diluting this mixture with demineralized water to 1 liter.

The fluid used to simulate environmentl conditions of the abomasum (at pH 2.9) is prepared by mixing 7.505 grams glycine with 5.85 grams sodium chloride and diluting this mixture with demineralized water to 1 liter. Eight parts of this solution are mixed with 2 parts of 0.1 normal hydrochloric acid for the test fluid.

The fluids are found to give reliable results in testing the pellets, according to similar experiments using actual rumen and abomasum fluid withdrawn from a ruminant.

EXAMPLE 1

Acid-sensitive dispersed phase particles are made by the following method. 250 Grams of magnesium phosphate are placed in a ball mill. 250 Grams of methylethylketone and 2.5 g. of stearic acid are also placed in the ball mill. This mixture is milled for 24 hr. to obtain a suspension of magnesium phosphate having a particle size of about 250 mesh.

EXAMPLE 2

100 Grams of 2-vinylpyridine, 2 g. of soap, 2 g. of potassium sulfate and 10 g. of divinylbenzene are dissolved or mixed with 1,000 g. of water. This mixture is tumbled in a water bath at 50° C. for 24 hr. to obtain a dispersion of crosslinked poly(2-vinylpyridine). The particle size of the dispersed crosslinked polymer is approximately 150 mμ. The polymer is separated from the water by spray drying the dispersion into heated air and collecting the dried polymer particles. It is found by contacting the dry powdered polymer with solvents such as toluene that the polymers are suspended to obtain the original particles as made in the emulsion polymerization. This test confirms the suitability of the crosslinked particles for use in the practice of this invention.

EXAMPLE 3

100 Grams of 2-methyl-5-vinylpyridine, 2 g. of soap, 2 g. of potassium persulfate are dissolved or mixed with 1,000 g. of water. This mixture is tumbled in a water bath at 50° C. to obtain a dispersion of poly(2-methyl-5-vinylpyridine) particles having approximately the diameter of 150 m$\mu$. This polymer dispersion is mixed with 25 g. of sodium sulfate to precipitate the dispersed polymer. The polymer is separated by filtering the liquid fraction from the precipitated polymer. After washing to remove residual salts, the precipitated polymer is dried to obtain a fine powder. A solution of the original particles is obtained by contacting the powder with organic liquids which are solvents for poly(2-methyl-5-vinylpyridine).

EXAMPLE 4 80 Grams of 2-methyl-5-vinylpyridine, 20 g. of styrene, 2 g. of soap, 2 g. of potassium persulfate and 8 g. of divinylbenzene are mixed in 1,000 g. of water. This mixture is tumbled at 60° C. for 24 hr. to obtain a dispersion of the crosslinked copolymer of 2-methyl-5-vinylpyridine and styrene. The particle size of the dispersion is about 150 m$\mu$. The purified dry polymer is obtained by precipitating the polymer from the dispersion by adding 20 g. of sodium sulfate. The precipitated polymer is filtered and the filter cake is washed to remove salts. The cake is then dried to obtain a fine powder of the crosslinked polymer.

EXAMPLE 5

100 Grams of diethylaminoethyl acrylate, 1 g. of Dupanol ME (an emulsifier marketed by Du Pont), 1 g. of Emulphor ON-870 (an emulsifier marketed by GAF Corp.), 15 g. of ethylene diacrylate, 1 g. of potassium persulfate and 0.5 g. of sodium bisulfite are mixed with 1,000 g. of water. This mixture is tumbled in a water bath at 60° C. for 24 hr. to obtain a dispersion of the crosslinked polymer. This polymer is separated from the dispersion in water as described in Example 4.

EXAMPLE 6

50 Grams of N,N-diethylaminoethyl methacrylate, 50 g. of methyl methacrylate, 1 g. of Dupanol ME, 1 g. of Emulphor ON-870, 6 g. of ethylene diacrylate, 1 g. of potassium persulfate, and 0.5 g. of sodium bisulfite are dissolved or mixed with 1,000 g. of water. This mixture is tumbled in a water bath at 60° C. for 24 hr. to obtain a crosslinked copolymer of methyl methacrylate and N,N-diethylaminoethyl acrylate. The crosslinked polymer is separated from the aqueous dispersion by the method described in Example 4.

EXAMPLE 7

250 Grams of aluminum phosphate is mixed with 250 g. of toluene and 5 g. of poly(methyl methacrylate) having an intrinsic viscosity of 0.25. This mixture is placed in the ball mill and milled for 24 hr. to obtain a finely divided aluminum phosphate protected from reaggregation by the dissolved polymethyl (methacrylate). The particle size of the polymer is in the range of about 250 mesh.

EXAMPLE 8

Ferric phosphate is ground by the same method as described in Example 7.

EXAMPLE 9

120 Grams of the magnesium phosphate dispersion described in Example 1 is mixed with 34 g. of poly(methyl methacrylate) dissolved in 500 g. of methylethylketone. Pellets composed of 90% methionine having a diameter of about 3 mm. are suspended by air in a fluidized bed and are sprayed with the above described coating mixture. The solvent is removed by the fluidizing air and the final product obtained is particles of methionine coated with poly(methyl methacrylate) containing therein dispersed magnesium phosphate. The coating thickness is about 6 mils and the coating weight, in this instance, is about 20% of the coated pellet weight. The resulting pellets are resistant to simulated conditions of the rumen but are readily made permeable at simulated abomasum conditions.

EXAMPLE 10

60 Grams of polystyrene having an intrinsic viscosity of 0.35 and 40 g. of the crosslinked poly(2-vinylpyridine) described in Example 2 are dissolved or suspended in 500 g. of trichloroethylene. Pellets composed of 75% lysine monohydrochloride, 15% magnesium carbonate and 10% binder having a diameter of approximately 3 mm. are suspended by air in a fluidized bed and while suspended are sprayed with this solution. The solvent is removed by the fluidizing air to obtain particles coated with about 6-mil layers of the polystyrene containing the dispersed crosslinked poly(2-vinylpyridine). The coated layer is resistant to simulated conditions of the rumen. However, when the coated pellets are exposed to simulated conditions of the abomasum, the film is permeated to an extent allowing the amino groups of the dispersed phased particles to react with the acidic groups. This reaction in turn causes the polymer particles to swell and thereby either cause the entire coating to become permeable or the swelling action even may disrupt the continuity of the coating itself. In either case, the core material comprising lysine is released and made available to the ruminant in the abomasum having resisted attack or penetration in the rumen.

EXAMPLE 11

30 Grams of the poly(2-methyl-5-vinylpyridine) described in Example 3 is dissolved in 200 g. of ethyl acetate. This solution is mixed with an additional 200 g. of ethyl alcohol containing therein dissolved 40 g. of poly(methacrylic acid) having an intrinsic viscosity of 0.05. Immediately on contact of the two solutions a precipitate is formed comprised of the polyelectrolyte complex between the acidic and basic polymers. This mixture is then reduced in particle size by ball milling for 36 hr. to obtain a dispersion of the polyelectrolyte complex wherein the individual particles have a diameter of about 100 mesh. This dispersion is then mixed with 100 g. of ethyl acetate containing dissolved therein 30 g. of poly(methyl methacrylate) having an intrinsic viscosity of 0.30. Pellets containing 90% threonine are fluidized as in Example 9 and 10 and the polymer coating mixture described above is applied as in Example 10.

The resulting coated pellets are tested, and found to resist penetration by simulated rumen fluid but are readily penetrated by simulated abomasum fluid.

EXAMPLE 12

50 Grams of the crosslinked poly(2-methyl-5-vinylpyridine), described in Example 4, is suspended by stirring in 125 g. of ethanol. This ethanol solution is then blended with 400 g. of a mixture composed of 850 g. of toluene and 100 g. of polystyrene having an intrinsic viscosity of 0.25. This final mixture is coated onto 3-mm. pellets composed of 90% threonine and 10% binders using a fluidized bed coating technique. The pellets coated with 12% by weight of coating resist penetration of simulated rumen fluid but readily permit entrance of water and solution of the threonine by simulated abomasum fluid. These coated pellets are suitable for feed supplement for ruminant animals where the absorption of the threonine takes place after the rumen.

The fluid used to simulate environmental conditions of the rumen (at pH 5.5) is prepared by mixing 11.397 grams of sodium acetate with 1.322 grams of acetic acid and diluting this mixture with demineralized water to 1 liter.

The fluid used to simulate environmental conditions of the abomasum (at pH 2.9) is prepared by mixing 7.505 grams glycine with 5.85 grams sodium chloride and diluting this mixture with demineralized water to 1 liter. Eight parts of this solution are mixed with two parts of 0.1 normal hydrochloric acid for the test fluid.

The fluids are found to give reliable results in testing the pellets, according to similar experiments using actual rumen and abomasum fluid withdrawn from a ruminant.

To be useful and practical as a feed for ruminants, it is considered that at least 60% and preferably at least 75% of the active ingredients of the core of the pellets to which this invention relates should be stable in the rumen and release in the abomasum.

Unless otherwise specified, all parts, ratios, percentages, etc., are by weight.

The invention has been described in detail with particular reference to certain preferred embodiments thereof, but it will be understood that variations and modifications can be effected within the spirit and scope of the invention.

I claim:

1. A pellet adapted for oral administration to a ruminant comprising a core material beneficial to the ruminant postruminally, and a coating surrounding said core material which protects the core material in the rumen and releases it in the abomasum, said coating comprising
   (a) a physiologically acceptable polymeric matrix insoluble in the environment of the rumen and abomasum consisting essentially of at least one polymer, copolymer, or blend of polymers or copolymers selected from the group consisting of cellulose esters, poly(vinylchloride), copolymers of vinylidene chloride, polystyrene, poly(methyl methacrylate), poly(dimethylsiloxane), polyesters made from dicarboxylic acids having from 8 to 22 carbon atoms and glycols having from 4 to 16 carbon atoms, polyamides from amino acids having from 8 to 22 carbon atoms or from dicarboxylic acids having from 8 to 22 carbon atoms condensed with diamines having from 4 to 16 carbon atoms, and polymethacrylates having silicone or fluorine substituted alcohol moieties of from 2 to 8 carbon atoms, and
   (b) a substance dispersed in said polymeric material which is stable in the environment of the rumen, but which leaches from said matrix below pH of about 4 in the environment of the abomasum thereby allowing said polymeric matrix to lose its integrity and release the core material,
   said coating comprising from about 35% to about 65% by volume of said dispersed substance, and said coating having a sticking temperature of at least about 50° C.

2. A pellet according to claim 1 wherein said polymeric matrix is selected from the group consisting of polystyrene, poly(vinylchloride), poly(methyl methacrylate) and esters of cellulose.

3. A pellet according to claim 1 wherein said dispersed substance is selected from the group consisting of magnesium phosphate, basic magnesium phosphate, aluminum phosphate, magnesium phosphite, ferrous phosphate, calcium phosphate, and polymers or copolymers having from 3 to 14% nitrogen or basic amino groups.

4. A pellet according to claim 1 wherein said core material is a nutrient for ruminants.

5. A pellet according to claim 4 wherein said core material is an amino acid.

6. A pellet according to claim 1 wherein said core material is a medicament for ruminants.

7. A method for preparing pellets adapted for oral administration to a ruminant having a core material beneficial to the ruminant postruminally, and a coating which renders said pellets resistant to the environment of the rumen but loses its integrity in the abomasum surrounding said core material, said method comprising mixing
   (a) from 35 to 65% by volume of a physiologically acceptable polymeric matrix insoluble in the environment of the rumen and abomasum consisting essentially of at least one polymer, copolymer, or blend of polymers or copolymers selected from the group consisting of poly(vinylchloride), vinylidene chloride, polystyrene, poly(methyl methacrylate), poly(dimethylsiloxane), polyesters made from dicarboxylic acids having from 8 to 22 carbon atoms and glycols having from 4 to 16 carbon atoms, polyamides from amino acids having from 8 to 22 carbon atoms or from dicarboxylic acids having from 8 to 22 carbon atoms condensed with diamines having from 4 to 16 carbon atoms and polymethacrylates having silicone or fluorine substituted alcohol moieties of from 2 to 8 carbon atoms, and
   (b) from 65 to 35% by volume of a substance which is stable in the environment of the rumen, but which is leachable from said matrix below pH of about 4 in the environment of the abomasum,
   and applying said coating composition to pellets to form a film, the weight of said coating accounting for from about 5 to about 50% of the total weight of the pellet, said coating having a sticking temperature of at least about 50° C.

* * * * *